(12) United States Patent
Thompson

(10) Patent No.: US 12,186,582 B2
(45) Date of Patent: Jan. 7, 2025

(54) TOUCHLESS-SWITCH SKIN SANITIZING SYSTEM-UVC FAR LIGHT

(71) Applicant: John William Thompson, Lancaster, PA (US)

(72) Inventor: John William Thompson, Lancaster, PA (US)

( * ) Notice: Subject to any disclaimer, the term of this patent is extended or adjusted under 35 U.S.C. 154(b) by 623 days.

(21) Appl. No.: 17/185,048

(22) Filed: Feb. 25, 2021

(65) Prior Publication Data

US 2022/0266057 A1    Aug. 25, 2022

(51) Int. Cl.
*A61N 5/06*  (2006.01)
*A61L 2/10*  (2006.01)

(52) U.S. Cl.
CPC .... *A61N 5/0624* (2013.01); *A61N 2005/0626* (2013.01); *A61N 2005/0642* (2013.01); *A61N 2005/0661* (2013.01)

(58) Field of Classification Search
CPC .......... A61N 5/0624; A61N 2005/0626; A61N 2005/0624; A61N 2005/0661; A61L 2/0047; A61L 2/10; A61L 9/20
See application file for complete search history.

(56) References Cited

U.S. PATENT DOCUMENTS

| | | | | |
|---|---|---|---|---|
| 4,786,812 A * | 11/1988 | Humphreys | ............... | A61L 9/20 250/455.11 |
| 4,952,369 A * | 8/1990 | Belilos | ...................... | A61L 2/10 422/24 |
| 6,953,940 B2 * | 10/2005 | Leighley | ................... | A61L 2/10 250/455.11 |
| 7,148,497 B2 * | 12/2006 | Gardner | ................ | G01J 3/0235 250/503.1 |
| 8,319,199 B2 * | 11/2012 | Garcia | ................. | H05B 3/0057 362/120 |
| 9,162,078 B2 * | 10/2015 | Irwin | ................... | A61N 5/0616 |
| 9,289,744 B2 * | 3/2016 | Garcia | ................... | B05D 3/067 |
| 9,610,372 B2 * | 4/2017 | St.Germain | ............... | A61L 2/10 |
| 10,058,711 B2 * | 8/2018 | Anderson | ........... | A61L 26/0066 |
| 10,786,586 B2 * | 9/2020 | Igarashi | .................... | A61L 2/10 |
| 10,842,895 B1 * | 11/2020 | Espina | ...................... | A61L 2/24 |
| 10,905,790 B1 * | 2/2021 | Moore | ....................... | A61L 2/10 |
| 2003/0015669 A1 * | 1/2003 | Janos | .................. | G03F 7/70575 250/492.2 |
| 2003/0018373 A1 * | 1/2003 | Eckhardt | .............. | A61N 5/0624 607/94 |
| 2004/0056201 A1 * | 3/2004 | Fink | ........................ | A61L 2/202 250/352 |
| 2005/0256554 A1 * | 11/2005 | Malak | .................. | A61N 5/0616 607/88 |

(Continued)

*Primary Examiner* — Sean M Luck
(74) *Attorney, Agent, or Firm* — Dunlap Bennett & Ludwig, PLLC

(57) ABSTRACT

A touchless skin sanitization system, device and method. The sanitizing device is configurable to sense an object and radiate the sensed object with UV light for a predetermined amount of time. A touchless switch activates the sanitizing device upon sensing the object, while a timer deactivates the sanitizing device after the predetermined amount of time. The sanitizing device provides an outer cover adapted to move between a closed condition and an open condition for maintenance. The outer cover is also adapted to mount the sanitizing device in a downward orientation relative to the UV radiating device.

5 Claims, 10 Drawing Sheets

(56) References Cited

U.S. PATENT DOCUMENTS

| | | | | |
|---|---|---|---|---|
| 2006/0004425 A1* | 1/2006 | Cumbie | ............... | A61N 5/0624 |
| | | | | 607/86 |
| 2008/0067418 A1* | 3/2008 | Ross | ........................ | A61L 2/24 |
| | | | | 250/455.11 |
| 2009/0143842 A1* | 6/2009 | Cumbie | ............... | A61N 5/0624 |
| | | | | 600/365 |
| 2009/0314308 A1* | 12/2009 | Kim | ...................... | A61L 2/0088 |
| | | | | 134/1 |
| 2015/0073396 A1* | 3/2015 | Randers-Pehrson | ........................ | |
| | | | | A61L 2/0047 |
| | | | | 607/88 |
| 2016/0008624 A1* | 1/2016 | Grossman | ............ | A61N 5/0603 |
| | | | | 607/92 |
| 2016/0030766 A1* | 2/2016 | Scritchfield | .......... | G06V 40/107 |
| | | | | 607/91 |
| 2016/0114067 A1* | 4/2016 | Dobrinsky | ......... | G01N 21/6486 |
| | | | | 250/461.1 |
| 2017/0290932 A1* | 10/2017 | Mori | ..................... | A61N 5/0613 |
| 2018/0055959 A1* | 3/2018 | Lin | ........................... | A61L 2/10 |
| 2018/0084956 A1* | 3/2018 | Childress | ................ | A61L 9/20 |
| 2018/0178032 A1* | 6/2018 | Pilcher | ................. | A61N 5/0616 |
| 2020/0215214 A1* | 7/2020 | Rosen | ..................... | A61L 2/084 |
| 2020/0254132 A1* | 8/2020 | Lee | ........................... | B60H 1/34 |
| 2020/0281686 A1* | 9/2020 | Finkelstein | ............ | A61B 46/20 |
| 2020/0397933 A1* | 12/2020 | Shin | ........................... | A61L 2/26 |
| 2020/0400296 A1* | 12/2020 | Rapisarda | ................ | F21L 4/00 |
| 2021/0010692 A1* | 1/2021 | Worrilow | .................. | F24F 8/22 |

\* cited by examiner

TOUCHLESS-SWITCH SKIN SANITIZING SYSTEM-UVC FAR LIGHT

BACKGROUND OF THE INVENTION

The present invention relates to sanitation systems and, more particularly, a touchless-switch skin sanitizing system configured to emit a dose of filtered ultraviolet C (UVC) light for safely sanitizing and deactivating pathogenic germs present on the skin, especially the skin of human hands. The present invention also provides a level of safety so that eyes are not exposed to UVC light source.

The skin is the human body's largest organ, colonized by innumerable microorganisms (viruses, bacteria, and fungi), most of which are harmless or even beneficial to their host. However, pathogenic germs also cover the surface of the skin. These pathogenic germs are what spread to surfaces, where the pathogenic germs contact a new host, resulting in contagion.

Current sanitation devices are not designed nor streamlined to target light source onto human hands. Furthermore, no timing methods are incorporated within their designs.

As can be seen, there is a need for a touchless-switch skin sanitizing system configured to emit a dose of filtered UVC light for safely sanitizing and deactivating pathogenic germs present on the skin, especially the skin of a user's hands, without using soap, water and/or chemicals.

The device embodied in the present invention safely sanitizes skin of hands using a touchless switch that enables the emission of predetermined doses of timed UVC light as a safe sanitizing agent, thereby adding another option to sanitize the skin of hands from known pathogens without using soap, water and/or chemicals.

The present invention includes the following method providing a specific dose of sanitizing agent to deactivate/sanitize pathogens from skin of hands. The sanitation process starts for a user by placing their hand(s) under the sanitizing device, whereby the device uses LED sensors that turns on UVC lighting, thus deactivating protein of pathogen germ(s) on the skin of the hands. An indicator provides a configurable timeframe that the UVC lighting remains on to deactivate contagions' protein. Once the UVC light turns off, the process of providing a suggested lighting dose is complete. The device is also adapted to address safety concerns associated with UVC light exposure during the sanitation process.

SUMMARY OF THE INVENTION

In one aspect of the present invention, a touchless sanitizing device includes the following: a control circuitry configurable to sense an object with a radiation field; an ultraviolet (UV) radiator electrically coupled to the control circuitry, wherein the UV radiator is configured to radiate a UV light across the radiation field; and a timer electrically coupled to the UV radiator, wherein the time deactivates the UV radiator after a predetermined amount of time.

In another aspect of the present invention, the touchless sanitizing device further includes an outer cover configured to move between a closed condition and an open condition; and the outer cover is configured to mount the sanitizing device to a supporting surface in such a way that the UV radiator is in a downward orientation relative to the object, wherein the control circuitry is configured to selectively set the predetermined time, and wherein the UV light is UV C light and/or Far UV light.

In yet another aspect of the present invention, a method of touchless hand sanitization includes the following: providing the above-mentioned touchless sanitizing device; mounting the outer cover to an upper supporting surface so that the radiation field is downwardly oriented relative to the upper supporting surface; and placing skin within the radiation field.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a touchless skin sanitization system, device, and method. The sanitizing device is configurable to sense an object and radiate the sensed object with UV light for a predetermined amount of time. A touchless switch activates the sanitizing device upon sensing the object, while a timer deactivates the sanitizing device after the predetermined amount of time. The sanitizing device provides an outer cover adapted to move between a closed condition and an open condition for maintenance. The outer cover is also adapted to mount the sanitizing device in a downward orientation relative to the UV radiating device.

Figure 1:
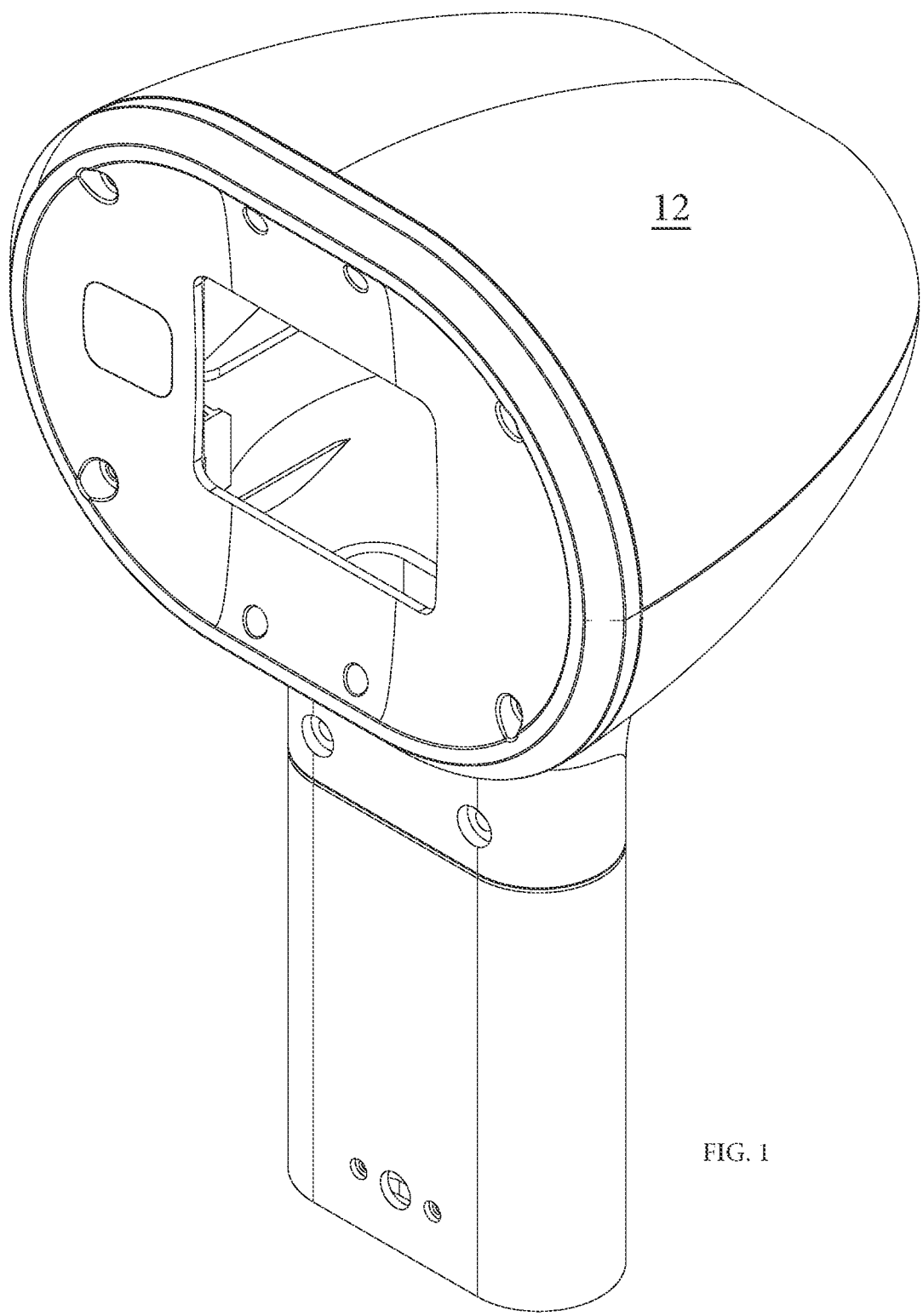
FIG. 1 is a top front perspective view of an exemplary embodiment of the present invention.
Figure 2:
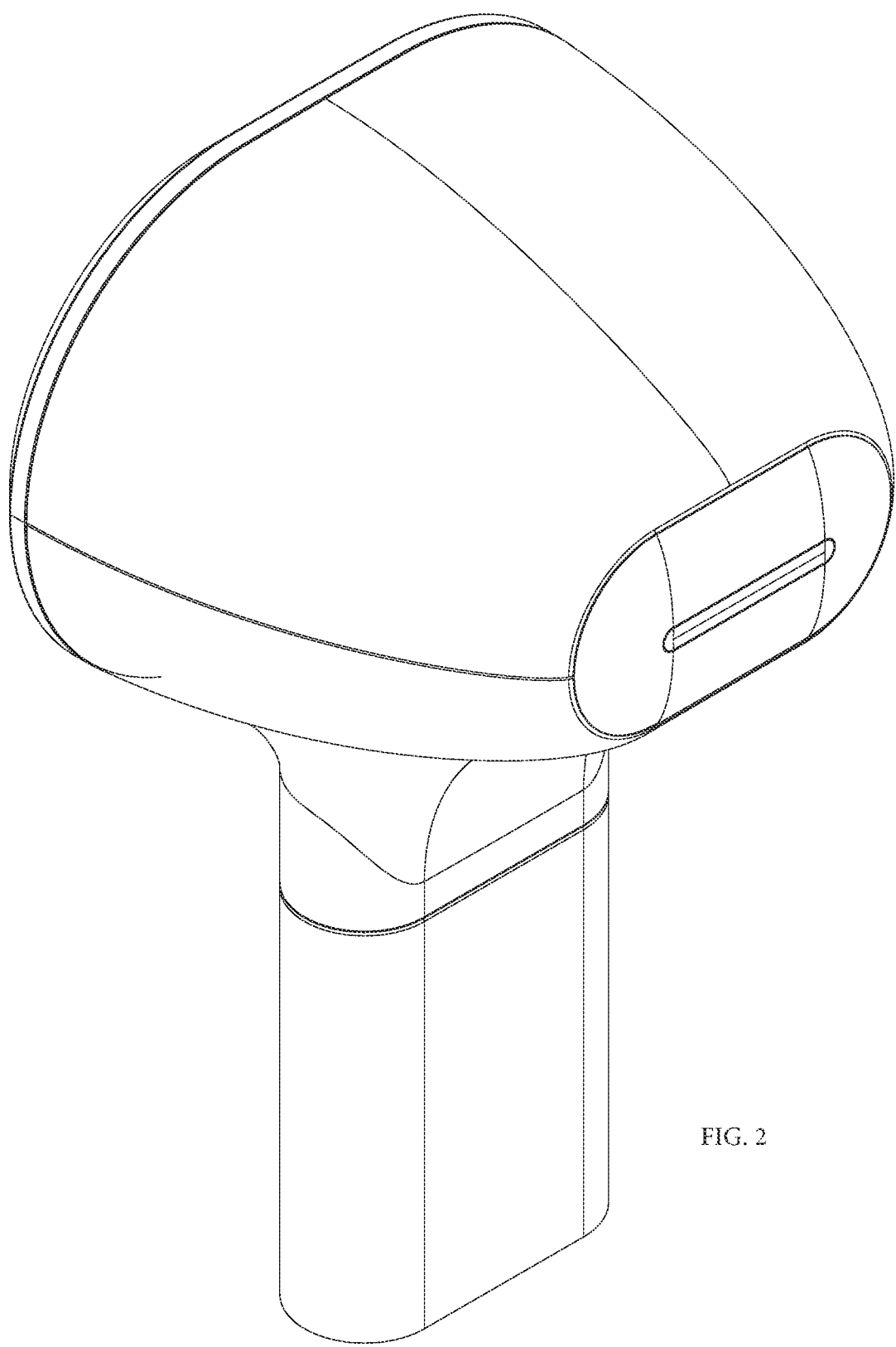
FIG. 2 is a top rear perspective view of an exemplary embodiment of the present invention.
Figure 3:
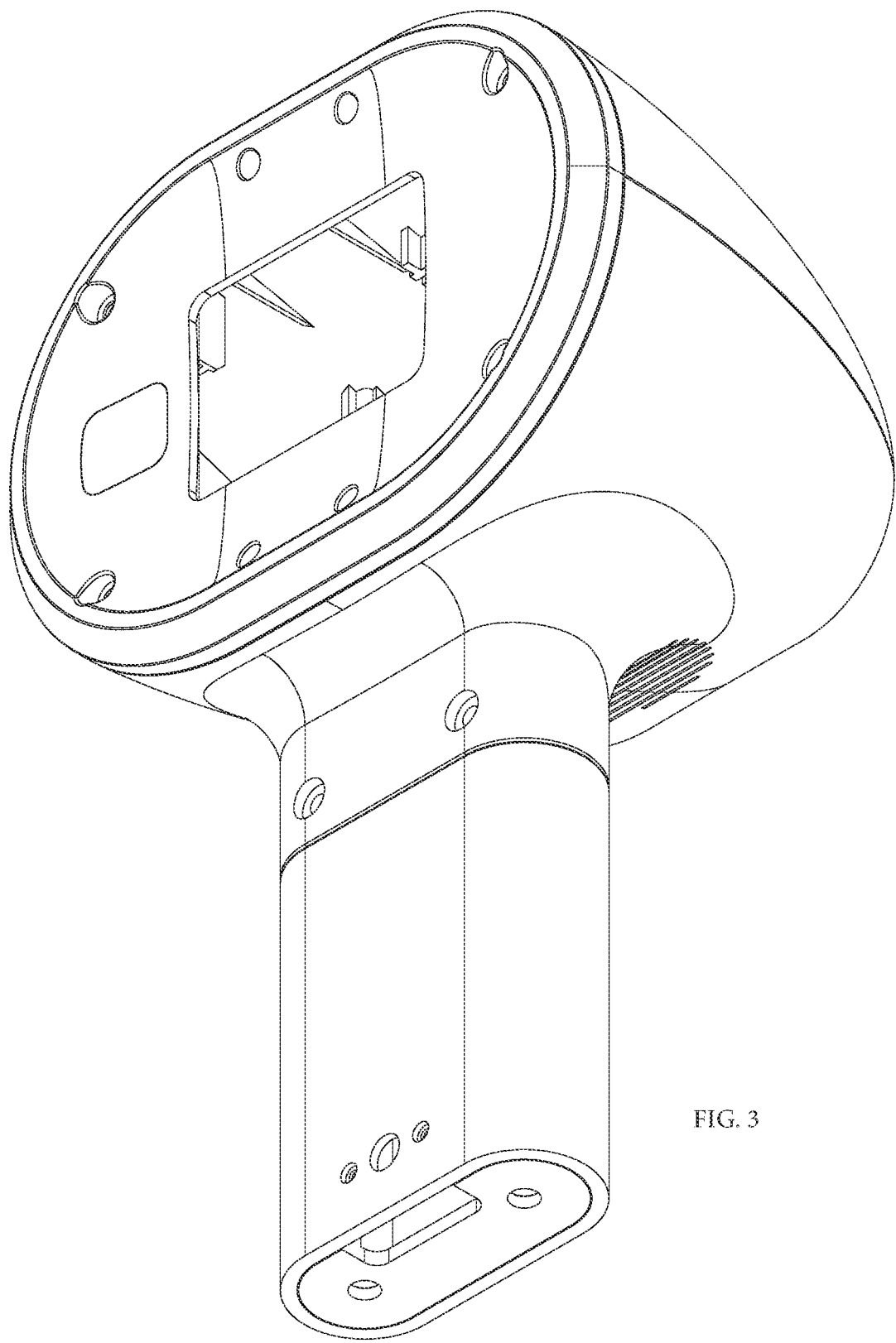
FIG. 3 is a bottom front perspective view of an exemplary embodiment of the present invention.
Figure 4:
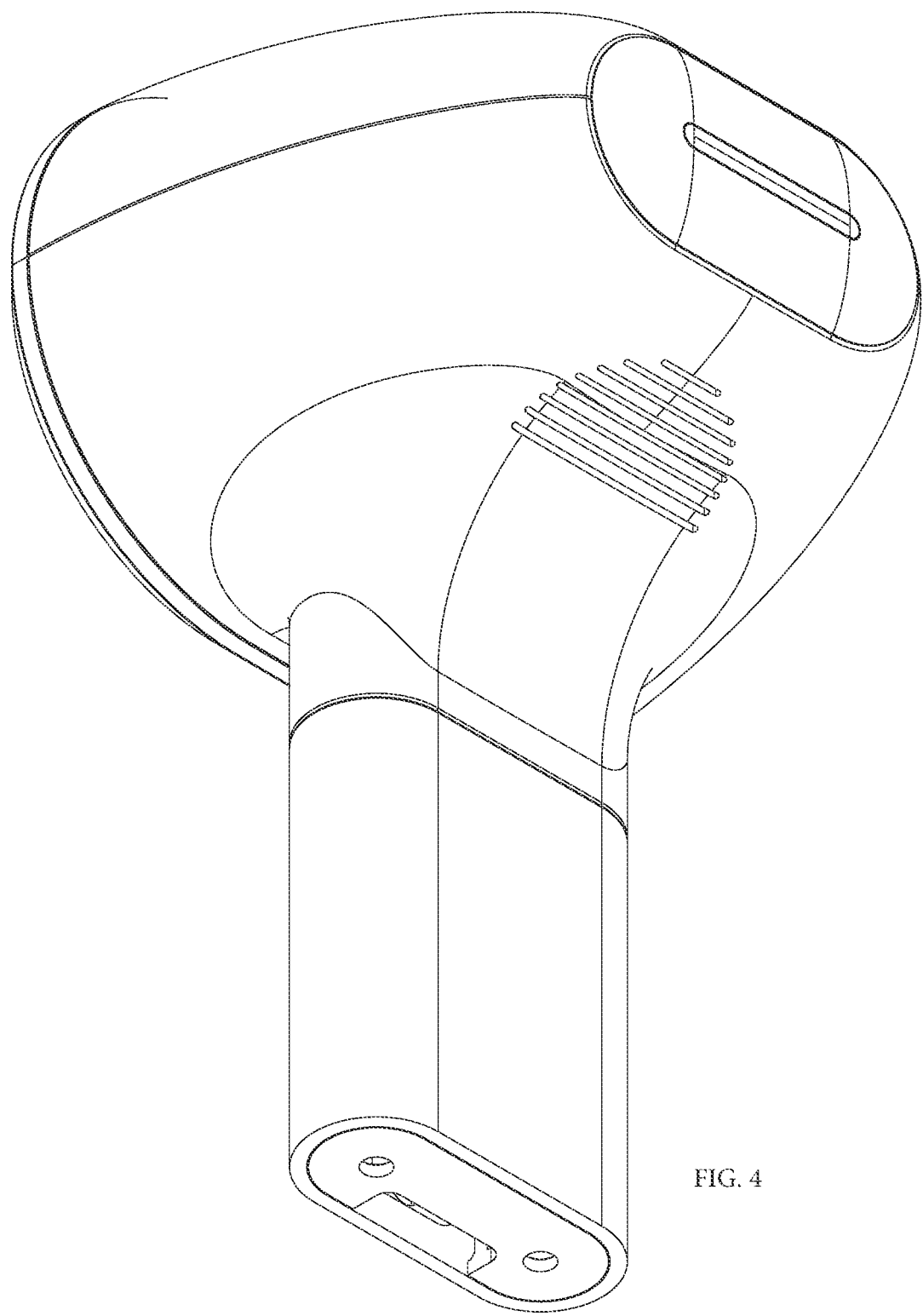
FIG. 4 is a bottom rear perspective view of an exemplary embodiment of the present invention.
Figure 5:
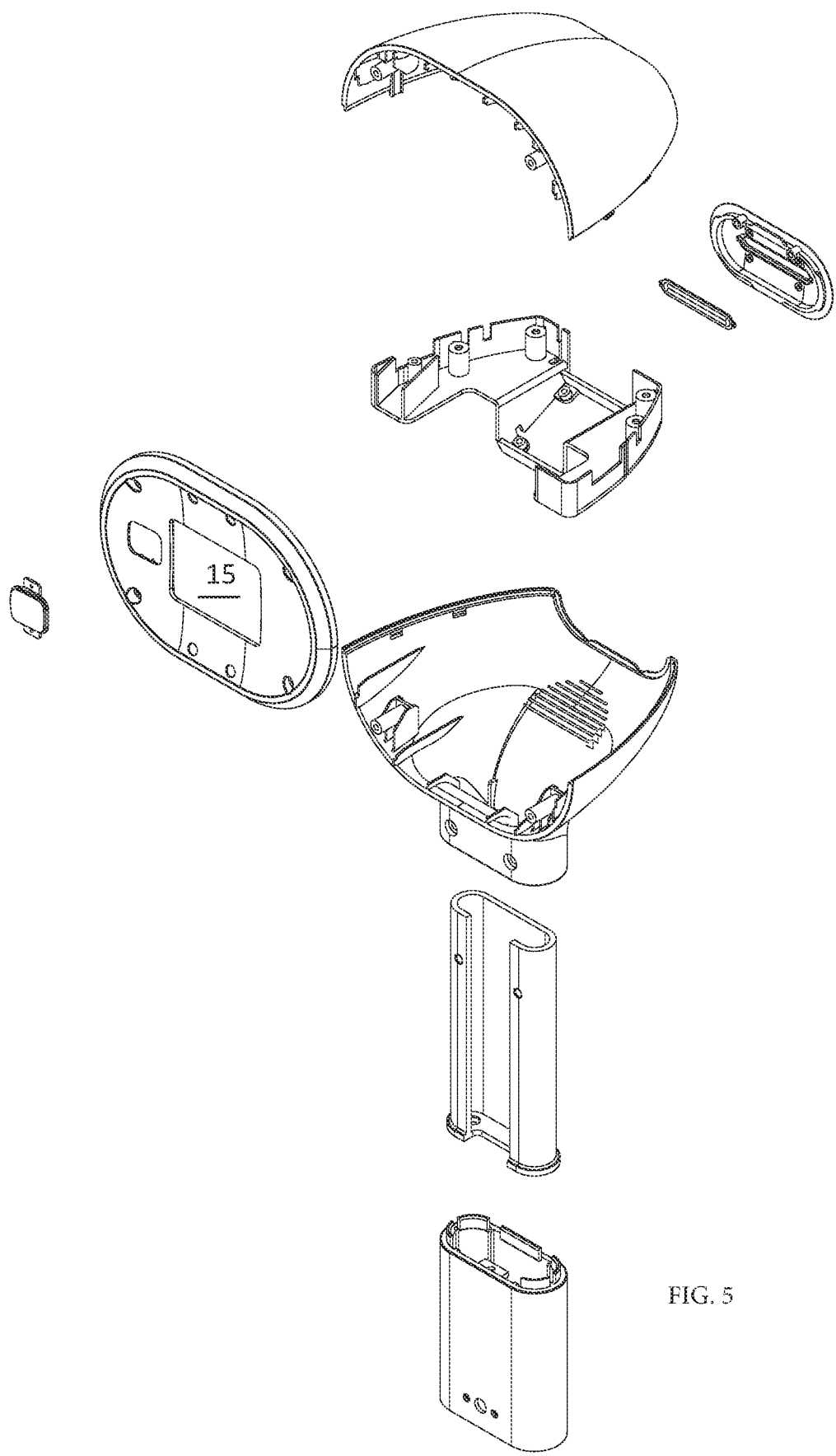
FIG. 5 is a top front exploded perspective view of an exemplary embodiment of the present invention.
Figure 6:
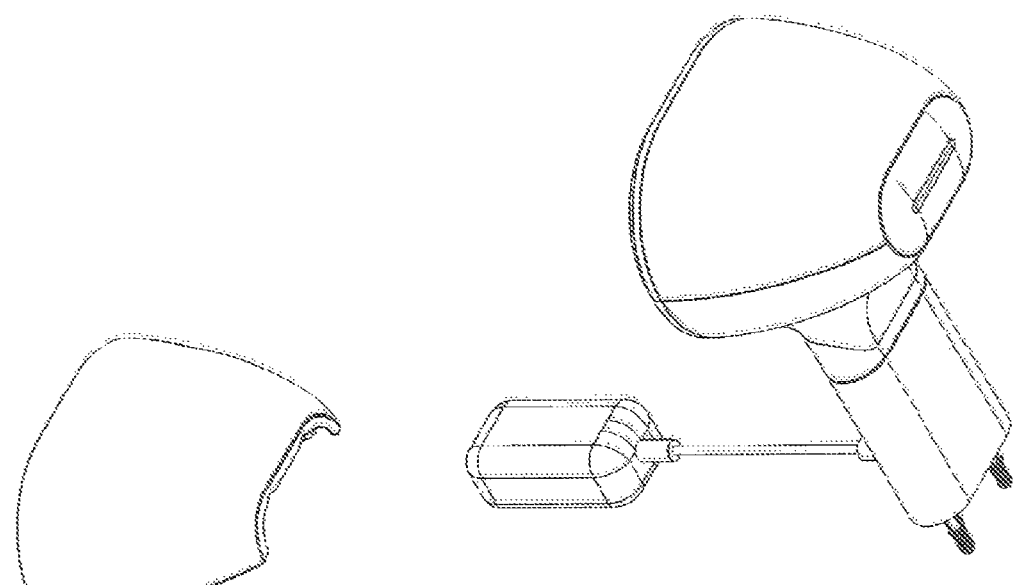
FIG. 6 is a rear perspective view of an exemplary embodiment of the present invention, illustrating the complete invention in its entirety.
Figure 7:
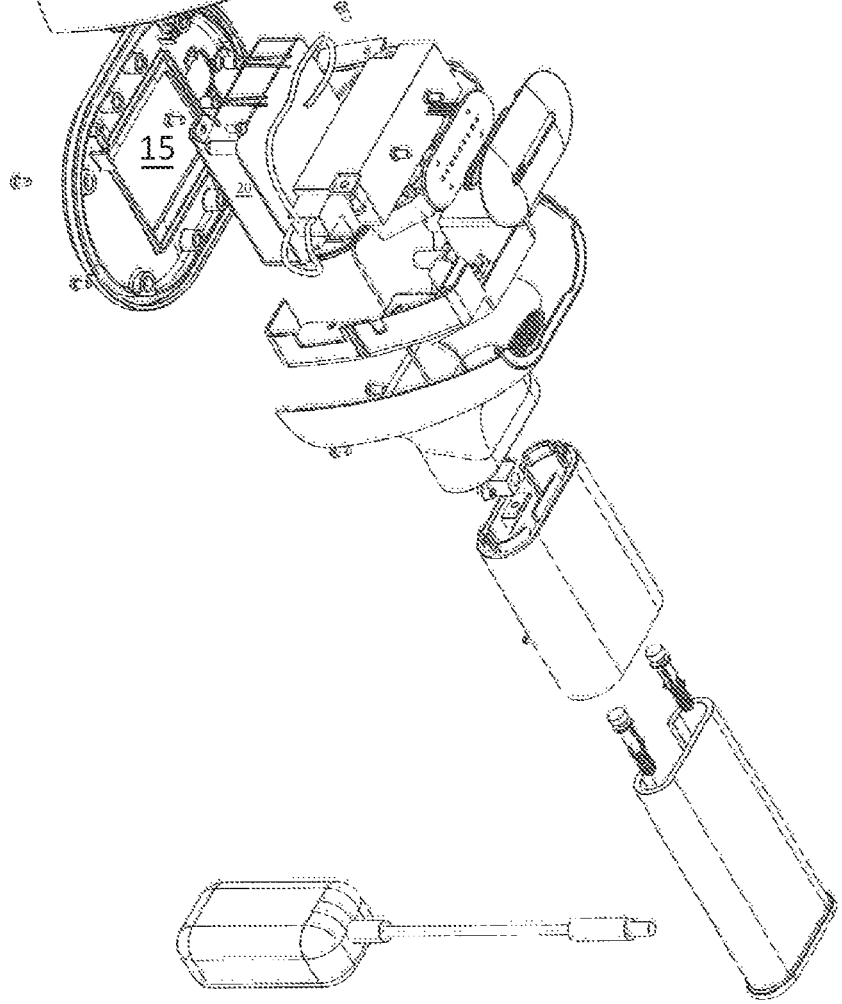
FIG. 7 is a top rear exploded perspective view of an exemplary embodiment of the present invention, shown in use.
Figure 8:
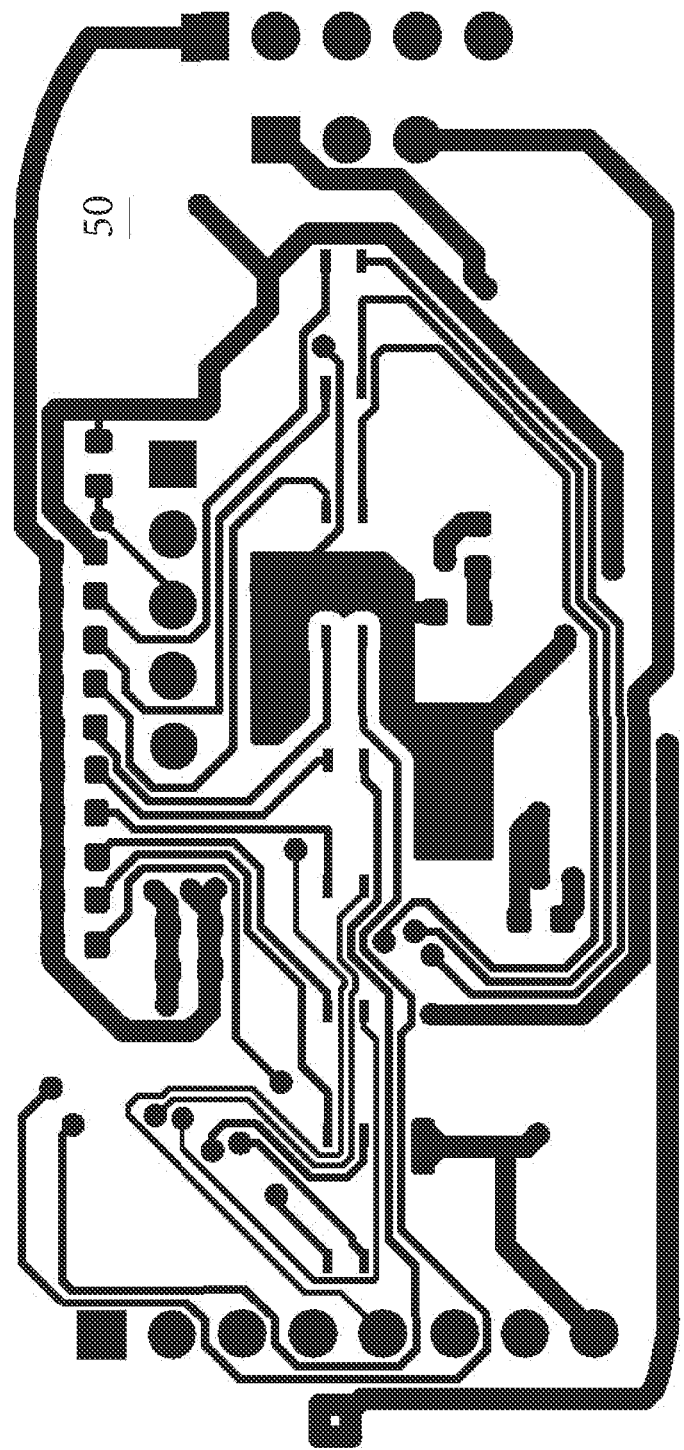
FIG. 8 is a schematic view of an exemplary embodiment of a control circuitry of the present invention.
Figure 9:
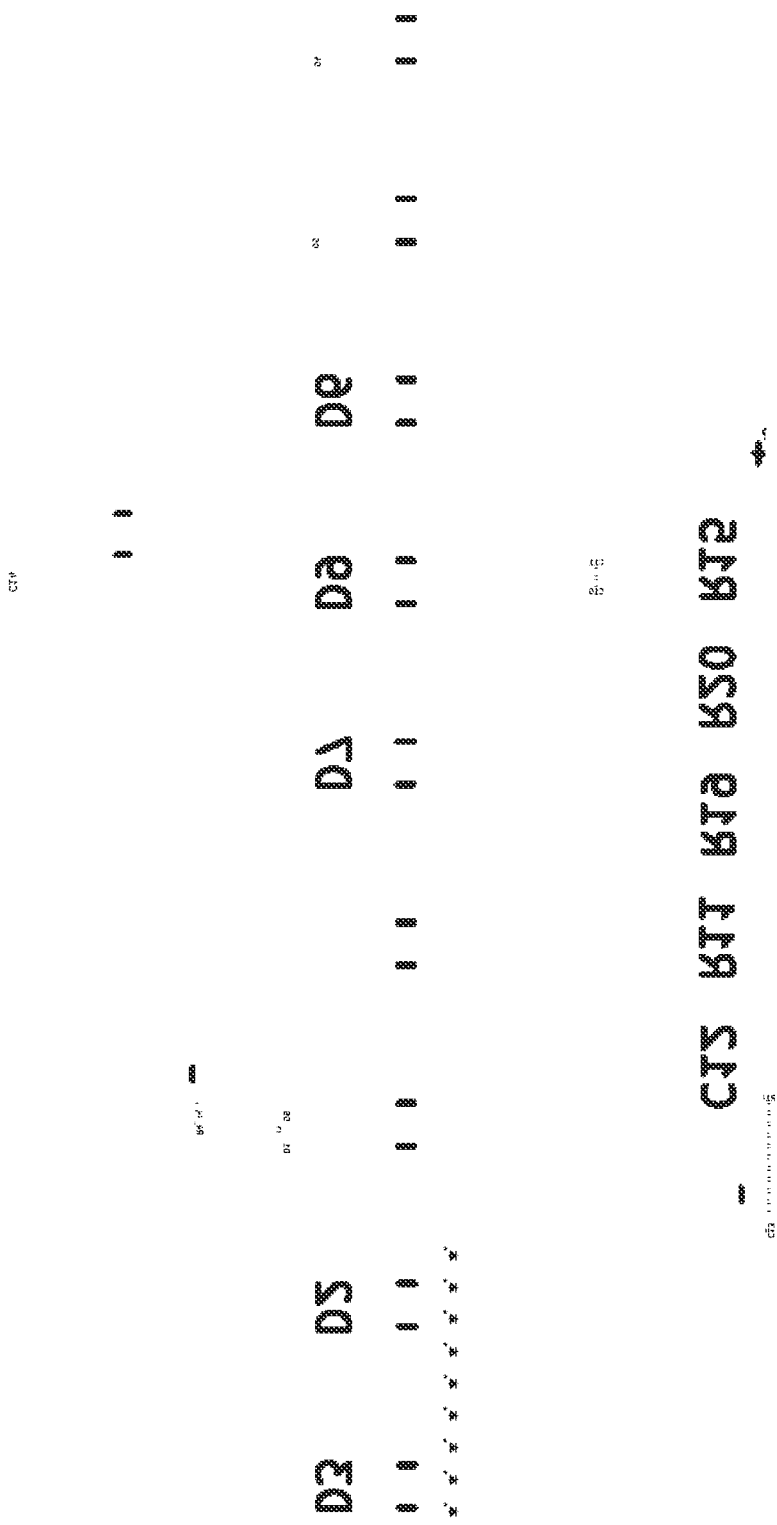
FIG. 9 is a schematic view of an exemplary embodiment of a control circuitry of the present invention.
Figure 10:
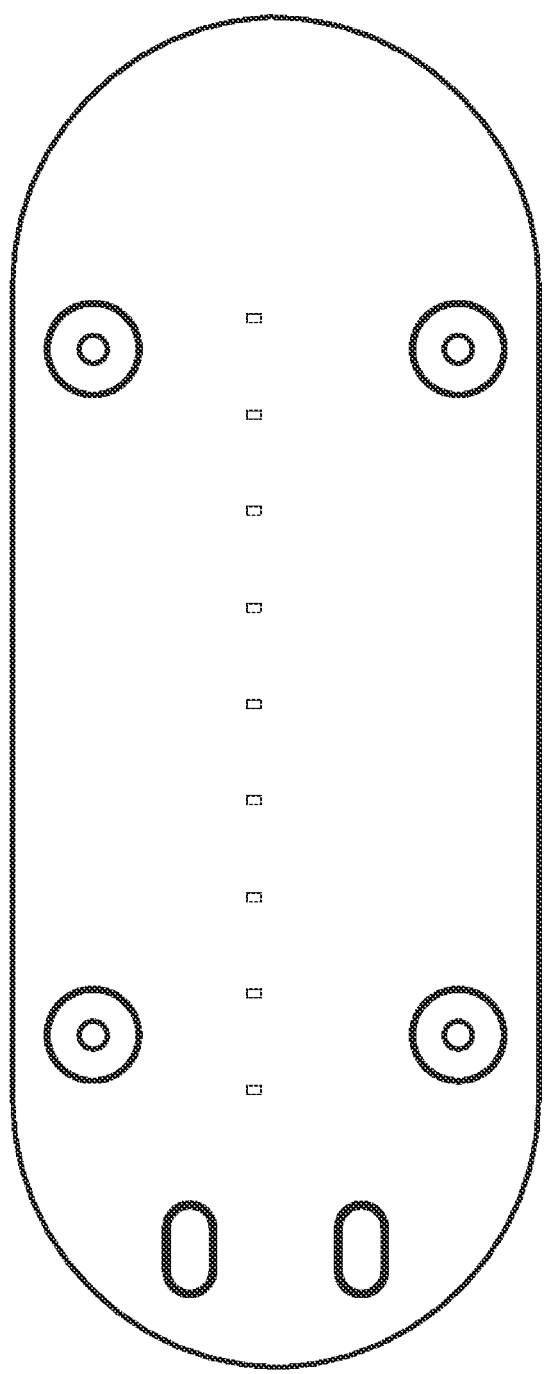
FIG. 10 is a schematic view of an exemplary embodiment of a control circuitry of the present invention.
Figure 11:
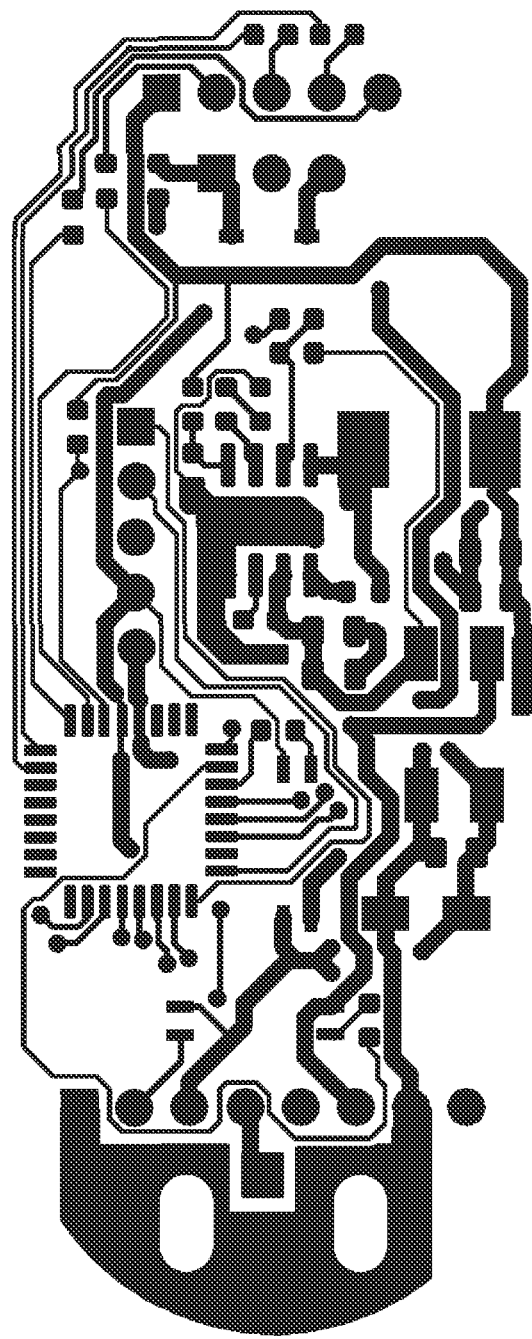
FIG. 11 is a schematic view of an exemplary embodiment of a control circuitry of the present invention.

Referring now to FIGS. 1 through 11, the present invention may include a touchless-switch skin sanitizing system configured to emit a dose of filtered ultraviolet C (UVC) light for safely sanitizing and deactivating pathogenic germs present on the skin, especially the skin of human hands. The sanitizing system embodies a sanitizing device 10.

The sanitizing device 10 may have an outer covering 12, which may be made of polyurethane/plastic or other suitable plasticized materials. The sanitizing device 10 may be operatively associated with a control circuitry 50 electrically coupled to an electronic command sensor board, to a software-command touchless switch, to a timer, and to a filtered UVC light component.

The sanitizing device 10 includes mechanical latches (see FIG. 5) that enable the outer covering 12 to move between a closed, operable condition and an opened, maintenance condition whereby the innards of sanitizing device 10 are accessible for maintenance. The sanitizing device 10 uses a UVC lighting component set inward from an emitting window 15 to shield eyes from UVC-Far light exposure.

Each component of the sanitizing device 10 has function for a specific task. The outside covering 12 is used to mount the sanitizing device 10 oriented in a downward position. The UVC-Far Light component 20 is used to sanitize/deactivate pathogens on skin of hands. The UVC may have a wavelength between 207-222 nanometers and may include Far ultraviolet (Far-UVC) light. The software electronic sensor board provides a touchless method for device to complete sanitizing process.

A method of using the present invention may include the following. The sanitizing device 10 disclosed above may be provided. A user may mount the sanitizing device 10 to a secure surface in the downward orientation. The user's hands are to be placed eight to nine inches underneath the sanitizing device 10 for a period of 10-30 seconds to complete sanitation process, deactivating pathogens from skin of hands. Potential future applications include sanitizing other areas of human body or the entire body.

The sanitizing device 10 is designed with hardware and software executing a specific time and method to deliver a configurable dose of UVC light to sanitize/deactivate pathogens on skin of hands for a selectable time. The systemic server and/or the computer of the present invention may each include computing systems. This disclosure contemplates any suitable number of computing systems. This disclosure contemplates the computing system taking any suitable physical form. As example and not by way of limitation, the computing system may be a virtual machine (VM), an embedded computing system, a system-on-chip (SOC), a single-board computing system (SBC) (e.g., a computer-on-module (COM) or system-on-module (SOM)), a desktop computing system, a laptop or notebook computing system, a smart phone, an interactive kiosk, a mainframe, a mesh of computing systems, a server, an application server, or a combination of two or more of these. Where appropriate, the computing systems may include one or more computing systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example and not by way of limitation, one or more computing systems may perform in real time or in batch mode one or more steps of one or more methods described or illustrated herein. One or more computing systems may perform at different times or at different locations one or more steps of one or more methods described or illustrated herein, where appropriate.

In some embodiments, the computing systems may execute any suitable operating system such as IBM's zSeries/Operating System (z/OS), MS-DOS, PC-DOS, MAC-OS, WINDOWS, UNIX, OpenVMS, an operating system based on LINUX, or any other appropriate operating system, including future operating systems. In some embodiments, the computing systems may be a web server running web server applications such as Apache, Microsoft's Internet Information Server™, and the like.

In particular embodiments, the computing systems include a processor, a memory, a user interface and a communication interface. In particular embodiments, the processor includes hardware for executing instructions, such as those making up a computer program. The memory includes main memory for storing instructions such as computer program(s) for the processor to execute, or data for processor to operate on. The memory may include mass storage for data and instructions such as the computer program. As an example and not by way of limitation, the memory may include an HDD, a floppy disk drive, flash memory, an optical disc, a magneto-optical disc, magnetic tape, a Universal Serial Bus (USB) drive, a solid-state drive (SSD), or a combination of two or more of these. The memory may include removable or non-removable (or fixed) media, where appropriate. The memory may be internal or external to computing system, where appropriate. In particular embodiments, the memory is non-volatile, solid-state memory.

The user interface includes hardware, software, or both providing one or more interfaces for communication between a person and the computer systems. As an example and not by way of limitation, an user interface device may include a keyboard, keypad, microphone, monitor, mouse, printer, scanner, speaker, still camera, stylus, tablet, touchscreen, trackball, video camera, another suitable user interface or a combination of two or more of these. A user interface may include one or more sensors. This disclosure contemplates any suitable user interface and any suitable user interfaces for them.

It should be understood, of course, that the foregoing relates to exemplary embodiments of the invention and that modifications may be made without departing from the spirit and scope of the invention as set forth in the following claims.

What is claimed is:

1. A touchless sanitizing device, comprising:
a control circuitry configurable to sense an object with a radiation field;
an ultraviolet (UV) radiator electrically coupled to the control circuitry, wherein the UV radiator is configured to radiate a UV light across the radiation field;
the control circuitry configured to activate the UV radiator when the object is sensed within the radiation field;
a timer electrically coupled to the UV radiator, wherein the time deactivates the UV radiator after a predetermined amount of time;
an outer cover configured to mount the touchless sanitizing device to a supporting surface in such a way that the radiation field encompasses an entire human body; and
the outer cover further comprising:
a rear portion defining a compartment housing the UV radiator;
the rear portion comprising a first rear portion and a second rear portion movable between a closed condition and an open condition providing access to inside the compartment for providing maintenance to components housed therein;
a front portion completely outside the compartment; the front portion circumscribing a void disposed along an outer surface of the front portion, wherein the UV radiator is set back from the void so that no other structural portion of the touchless sanitizing device directly touches the void or protrudes through the void, whereby eyes of a bystander were shielded from the UV light by the front portion; and a plurality of mechanical latches disposed along the first and second rear portions for effectuating the closed condition and the open condition that enables the front portion to be separated from the rear portion.

2. The touchless sanitizing device of claim 1, wherein the control circuitry is configured to selectively set the predetermined time.

3. The touchless sanitizing device of claim 2, wherein the UV light is UV C light range of 207-222 nms.

4. The touchless sanitizing device of claim 2, wherein the UV light is Far UV light.

5. A method of touchless hand sanitization, the method comprising:

providing a touchless sanitizing device of claim 2;

mounting the outer cover to an upper supporting surface so that the radiation field is downwardly oriented relative to the upper supporting surface; and placing skin within the radiation field.

\* \* \* \* \*